US012623991B2

(12) United States Patent
Weber et al.

(10) Patent No.: US 12,623,991 B2
(45) Date of Patent: May 12, 2026

(54) REMOVAL OF ALDEHYDES IN ACETIC ACID PRODUCTION

(71) Applicant: LyondellBasell Acetyls, LLC, Houston, TX (US)

(72) Inventors: Shane J. Weber, League City, TX (US); Noel C. Hallinan, Loveland, OH (US); Ryan J. Mathews, Tomball, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 535 days.

(21) Appl. No.: 18/109,414

(22) Filed: Feb. 14, 2023

(65) Prior Publication Data

US 2023/0257335 A1      Aug. 17, 2023

Related U.S. Application Data

(60) Provisional application No. 63/309,928, filed on Feb. 14, 2022.

(51) Int. Cl.
| | |
|---|---|
| *C07C 51/46* | (2006.01) |
| *B01D 3/14* | (2006.01) |
| *B01D 5/00* | (2006.01) |
| *B01J 19/24* | (2006.01) |
| *B01J 31/08* | (2006.01) |

(52) U.S. Cl.
CPC ............. *C07C 51/46* (2013.01); *B01D 3/143* (2013.01); *B01D 5/006* (2013.01); *B01J 19/245* (2013.01); *B01J 31/08* (2013.01)

(58) Field of Classification Search
CPC .......... C07C 51/46; B01D 3/143; B01D 5/006
See application file for complete search history.

(56) References Cited

U.S. PATENT DOCUMENTS

| | | |
|---|---|---|
| 5,416,237 A | 5/1995 | Aubigne et al. |
| 5,620,567 A | 4/1997 | Seidel et al. |
| 5,817,869 A | 10/1998 | Hinnenkamp et al. |
| 5,932,764 A | 8/1999 | Morris et al. |
| 6,143,930 A | 11/2000 | Singh et al. |
| 6,339,171 B1 | 1/2002 | Singh et al. |

(Continued)

FOREIGN PATENT DOCUMENTS

| | | |
|---|---|---|
| EP | 0487284 A2 | 5/1992 |
| EP | 0645362 A1 | 3/1995 |

(Continued)

OTHER PUBLICATIONS

Sumit Kamal et al., Kinetic Study for Oligomerization of Acetaldehyde over Cation Exchange Resin; Applied Catalysis A, General, 608 (2020) 117841; 2020 Published by Elsevier B.V.

(Continued)

*Primary Examiner* — Yate' K Cutliff

(57) ABSTRACT

A system and method for removing acetaldehyde from an acetic acid system, including providing a solution from the acetic acid system, the stream having methyl iodide and acetaldehyde, distilling the solution to produce an overhead stream having a higher concentration of acetaldehyde, contacting the overhead stream, and optionally a hydroxyl compound, with an acid catalyst to convert the acetaldehyde to an aldehyde derivative having a higher boiling point than acetaldehyde.

11 Claims, 2 Drawing Sheets

(56)     References Cited

U.S. PATENT DOCUMENTS

| | | | |
|---|---|---|---|
| 6,552,221 B1 | 4/2003 | Hallinan et al. | |
| 7,524,988 B2 * | 4/2009 | Harris ................... | C07C 51/487 |
| | | | 562/608 |
| 7,683,212 B2 | 3/2010 | Kojima et al. | |
| 7,790,919 B2 | 9/2010 | Hallinan et al. | |
| 8,076,512 B2 | 12/2011 | Fitzpatrick et al. | |
| 8,969,613 B2 | 3/2015 | Hallinan et al. | |
| 8,969,988 B2 | 3/2015 | Ikeda et al. | |
| 9,790,159 B2 | 10/2017 | Hallinan et al. | |
| 9,873,655 B2 | 1/2018 | Hallinan et al. | |
| 9,908,833 B2 | 3/2018 | Hallinan et al. | |
| 10,428,005 B2 | 10/2019 | Shimizu | |
| 10,550,058 B2 | 2/2020 | Shimizu | |
| 10,584,087 B2 | 3/2020 | Hallinan et al. | |
| 2020/0079719 A1 * | 3/2020 | Shimizu ................. | C07C 51/48 |

FOREIGN PATENT DOCUMENTS

| | | | |
|---|---|---|---|
| JP | 3306227 B2 | 7/2002 | |
| WO | 2020205997 A1 | 10/2020 | |

OTHER PUBLICATIONS

The International Search Report and Written Opinion for PCT/US2023/012995 mailed Jun. 19, 2023.

* cited by examiner

REMOVAL OF ALDEHYDES IN ACETIC ACID PRODUCTION

PRIOR RELATED APPLICATIONS

This application claims the benefit of priority to U.S. Provisional Application No. 63/309,928, filed on Feb. 14, 2022, the contents of which are incorporated herein by reference in their entirety.

FIELD OF THE INVENTION

This disclosure relates to the production of acetic acid. More particularly, the disclosure relates to removal of acetaldehyde in acetic acid production.

BACKGROUND OF THE INVENTION

In the current acetic acid production process, a reaction mixture is withdrawn from a reactor and is separated in a flash tank into a liquid fraction and a vapor fraction comprising acetic acid generated during the carbonylation reaction. The liquid fraction may be recycled to the carbonylation reactor, and the vapor fraction is passed to a separations unit, which by way of example may be a light-ends distillation column. The light-ends distillation column separates a crude acetic acid product from other components. The crude acetic acid product is passed to a drying column to remove water and then is subjected to further separations to recover acetic acid.

One challenge facing the industry is the presence of aldehyde(s) in acetic acid production, which can be present in the feed and also form as an undesired byproduct of carbonylation reactions. Processes for removing aldehydes exist; however, there continues to be a need to improve upon, and provide alternatives to, current aldehyde removal processes.

SUMMARY OF THE INVENTION

An aspect of the disclosure relates to a method for removing acetaldehyde from an acetic acid system, including: providing a solution from the acetic acid system, the solution comprising methyl iodide and acetaldehyde; distilling the solution to produce an overhead stream having a higher concentration of acetaldehyde, and contacting the overhead stream, and optionally a hydroxyl compound, with an acid catalyst to convert the acetaldehyde to an aldehyde derivative having a higher boiling point that acetaldehyde.

Another aspect of the disclosure relates to a method of operating an acetic acid production system, including: flashing a reaction mixture discharged from an acetic acid production reactor into a vapor stream and a liquid stream, the vapor stream comprising acetic acid, water, methanol, methyl acetate, methyl iodide, and acetaldehyde; distilling the vapor stream into a product stream of acetic acid and water, a first bottoms stream, and a first overhead stream comprising methyl iodide, water, methyl acetate, acetic acid, and acetaldehyde; condensing the first overhead stream into a light aqueous phase comprising water, acetic acid, and methyl acetate, and a heavy organic phase comprising methyl iodide, acetic acid, water, and acetaldehyde; distilling a portion of the light aqueous phase and/or a portion of the heavy organic phase to produce a second overhead stream comprising a higher concentration of acetaldehyde than the corresponding distillation feed stream; and contacting the second overhead stream with an acid catalyst to convert at least a portion of the acetaldehyde to an aldehyde derivative having a higher boiling point than acetaldehyde.

Yet another aspect relates to a method of producing acetic acid, including: reacting methanol and carbon monoxide in the presence of a carbonylation catalyst to produce a crude stream comprising acetic acid; flashing the crude stream discharged from an acetic acid production reactor into a vapor stream and a liquid stream, the vapor stream comprising acetic acid, water, methanol, methyl acetate, methyl iodide, and acetaldehyde; distilling the vapor stream into a product stream of acetic acid and water, a first bottoms stream, and a first overhead stream comprising methyl iodide, water, methyl acetate, acetic acid, and acetaldehyde; condensing the first overhead stream into a light aqueous phase comprising water, acetic acid, and methyl acetate, and a heavy organic phase comprising methyl iodide, acetic acid, water, and acetaldehyde; distilling a portion of the light aqueous phase and/or a portion of the heavy organic phase to produce a second overhead stream comprising a higher concentration of acetaldehyde than the corresponding distillation feed stream; and contacting the second overhead stream with an acid catalyst to convert at least a portion of the acetaldehyde to an aldehyde derivative having a higher boiling point than acetaldehyde.

Yet another aspect of the disclosure relates to an acetic acid production system, having: a reactor to react methanol and carbon monoxide in the presence of a carbonylation catalyst to form acetic acid; a flash vessel that receives a reaction mixture comprising the acetic acid from the reactor; a first distillation column that receives a vapor stream from the flash vessel; a decanter that receives a condensed overhead stream from the distillation column; a second distillation column that receives a portion of a heavy organic phase stream and/or a portion of a light aqueous phase stream from the decanter; an acetaldehyde reactor that receives (1) a second condensed overhead stream, comprising methyl iodide and acetaldehyde, from the second distillation column and (2) optionally a hydroxyl compound, wherein the acetaldehyde reactor comprises an acid catalyst to convert at least a portion of the acetaldehyde to an aldehyde derivative having a higher boiling point than acetaldehyde.

Yet another aspect of the disclosure relates to an acetic acid production system, having: an acetic acid production reactor to react methanol and carbon monoxide in the presence of a carbonylation catalyst to form acetic acid; a flash vessel that receives a reaction mixture comprising the acetic acid from the reactor; a first distillation column that receives a vapor stream from the flash vessel; a decanter that receives a condensed first overhead stream from the distillation column; a second distillation column that receives a portion of a heavy organic phase stream or a portion of a light aqueous phase stream from the decanter; an acetaldehyde reactor that receives (1) a second condensed overhead stream, comprising methyl iodide and acetaldehyde, from the second distillation column and (2) optionally a hydroxyl compound, wherein the acetaldehyde reactor comprises an acid catalyst to convert at least a portion of the acetaldehyde to an aldehyde derivative having a higher boiling point than acetaldehyde; and a third distillation column that receives an effluent from the acetaldehyde reactor.

The above paragraphs present a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF THE DRAWINGS

The claimed subject matter may be understood by reference to the following description taken in conjunction with the accompanying drawings, in which like reference numerals identify like elements, and in which:

While the disclosed process and system are susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

A detailed description of embodiments of the disclosed process follows. However, it is to be understood that the described embodiments are merely exemplary of the process and that the process may be embodied in various and alternative forms of the described embodiments. Therefore, specific procedural, structural and functional details which are addressed in the embodiments described herein are not to be interpreted as limiting, but merely as a basis for the claims and as a representative basis for teaching one skilled in the art to variously employ the disclosed process.

The designation of groups of the Periodic Table of the Elements as used herein is in accordance with the current IUPAC convention. The expression "HAc" is used herein as an abbreviation for acetaldehyde. The expression "MeI" is used herein as an abbreviation for methyl iodide. The expression "HI" is used herein as an abbreviation for hydrogen iodide. The expression "acac" is used herein as an abbreviation for acetoacetate anion, i.e., $H_3CC(=O)CH_2C(=O)O—$. Unless specifically indicated otherwise, the expression "wt %" as used herein refers to the percentage by weight of a particular component in the referenced composition. With respect to all ranges disclosed herein, such ranges are intended to include any combination of the mentioned upper and lower limits even if the particular combination is not specifically listed.

Embodiments of the disclosed process and system involve the production of acetic acid by carbonylating methanol in a carbonylation reaction. The carbonylation reaction may be represented by: $CH_3OH + CO \rightarrow CH_3COOH$ Embodiments of the disclosed process include: (a) obtaining HI in an acetic acid production system; and (b) continuously introducing a complexing agent into the system, wherein the complexing agent and HI interact to form a complex. The following description elaborates upon the disclosed process.

Acetic Acid Production

Figure 1:
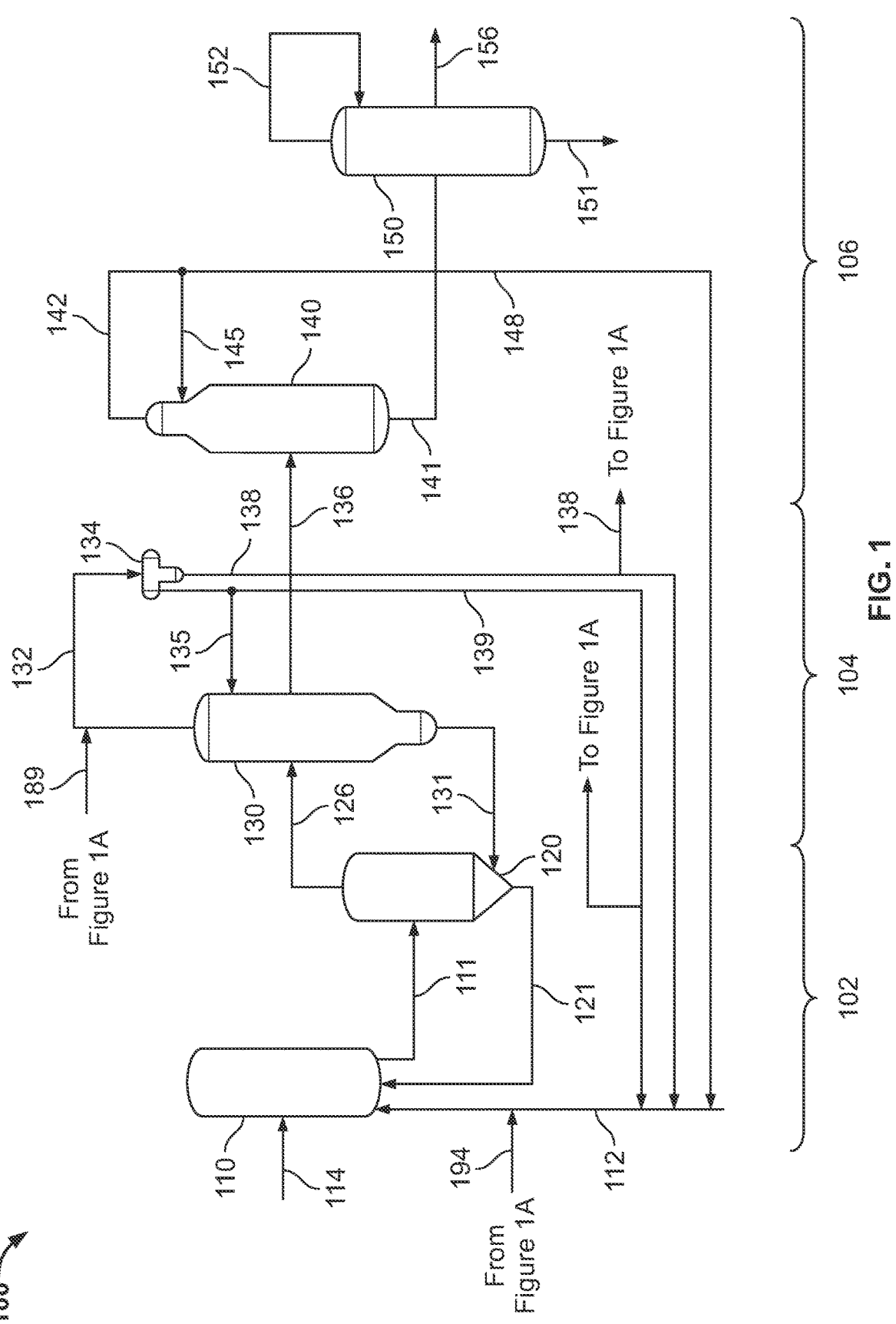
FIG. 1 is a schematic of an exemplary acetic acid production system in accordance with embodiments of the present techniques.

FIG. 1 is a schematic of an exemplary acetic acid production system 100 implementing the carbonylation reaction. In certain embodiments, the acetic acid system 100 may include a reaction area 102, a light-ends area 104, and a purification area 106. The reaction area 102 may include a reactor 110, a flash vessel 120, and associated equipment. The reactor 110 is a reactor or vessel in which methanol is carbonylated in the presence of a catalyst to form acetic acid at elevated pressure and temperature.

The flash vessel 120 is a tank or vessel in which a reaction mixture obtained in the reactor is at least partially depressurized and/or cooled to form a vapor stream and a liquid stream. The liquid stream 121 may be a product or composition which has components in the liquid state under the conditions of the processing step in which the stream is formed. The vapor stream 126 may be a product or composition which has components in the gaseous state under the conditions of the processing step in which the stream is formed.

The light-ends area 104 may include a separations column, for example a light-ends column 130, and associated equipment such as decanter 134. The light-ends column is a fractioning or distillation column and includes equipment associated with the column, such as heat exchangers, decanters, pumps, compressors, valves, and the like. The purification area 106 may include a drying column 140, optionally a heavy-ends column 150, and associated equipment, and so on. The heavy-ends column is a fractioning or distillation column and includes any equipment associated with the column, such as heat exchangers, decanters, pumps, compressors, valves, and the like. Further, as discussed below, various recycle streams may include streams 121, 138, 139, and 148. The recycle streams may be products or compositions recovered from a processing step downstream of the flash vessel 120 and which is recycled to the reactor 110, flash vessel 120, or light-ends column 130, and so forth.

In an embodiment, the reactor 110 may be configured to receive a carbon monoxide feed stream 114 and a methanol feed stream 112. A reaction mixture may be withdrawn from the reactor in stream 111. Other streams may be included such as, for example, a stream that may recycle a bottoms mixture of the reactor 110 back into the reactor 110, or a stream may be included to release a gas from the reactor 110.

In an embodiment, the flash vessel 120 may be configured to receive stream 111 from the reactor 110. In the flash vessel 120, stream 111 may be separated into a vapor stream 126 and a liquid stream 121. The vapor stream 126 may be communicated to the light-ends column 130, and the liquid stream 121 may be communicated to the reactor 110. In an embodiment, stream 126 may have acetic acid, water, methyl iodide, methyl acetate, HI, mixtures thereof and the like.

In an embodiment, the light-ends column 130 may be a distillation column and associated equipment such as a decanter 134, pumps, compressors, valves, and other related equipment. The light-ends column 130 may be configured to receive stream 126 from the flash vessel 120. In the illustrated embodiment, stream 132 is the overhead product from the light-ends column 130, and stream 131 is bottoms product from the light-ends column 130. As indicated, light-ends column 130 may include a decanter 134, and stream 132 may pass into decanter 134.

Stream 135 may emit from decanter 134 and recycle back to the light-ends column 130. Stream 138 may emit from decanter 134 and may recycle back to the reactor 110 via, for example, stream 112 or be combined with any of the other streams that feed the reactor. Stream 139 may recycle a portion of the light phase of decanter 134 back to the reactor 110 via, for example, stream 112. Stream 136 may emit from the light-ends column 130. Other streams may be included such as, for example, a stream that may recycle a bottoms mixture of the light-ends column 130 back into the light-ends column 130. Streams received by or emitted from the light-ends column 130 may pass through a pump, compressor, heat exchanger, and the like as is common in the art.

In an embodiment, the drying column 140 may be a vessel and associated equipment such as heat exchangers, decanters, pumps, compressors, valves, and the like. The drying column 140 may be configured to receive stream 136 from the light-ends column 130. The drying column 140 may separate components of stream 136 into streams 142 and 141. Stream 142 may emit from the drying column 140, recycle back to the drying column via stream 145, and/or recycle back to the reactor 110 through stream 148 (via, for example, stream 112). Stream 141 may emit from the drying column 140 and may include de-watered crude acetic acid product. Stream 142 may pass through equipment such as, for example, a heat exchanger or separation vessel before streams 145 or 148 recycle components of stream 142. Other streams may be included such as, for example, a stream may recycle a bottoms mixture of the drying column 140 back into the drying column 140. Streams received by or emitted from the drying column 140 may pass through a pump, compressor, heat exchanger, separation vessel, and the like as is common in the art.

The heavy-ends column 150 may be a distillation column and associated equipment such as heat exchangers, decanters, pumps, compressors, valves, and the like. The heavy-ends column 150 may be configured to receive stream 141 from the drying column 140. The heavy-ends column 150 may separate components from stream 141 into streams 151, 152, and 156. Streams 151 and 152 may be sent to additional processing equipment (not shown) for further processing. Stream 152 may also be recycled, for example, to light-ends column 140. Stream 156 may have acetic acid product.

A single column (not depicted) may be used in the place of the combination of the light-ends distillation column 130 and the drying column 140. The single column may vary in the diameter/height ratio and the number of stages according to the composition of vapor stream from the flash separation and the requisite product quality. For instance, U.S. Pat. No. 5,416,237, the teachings of which are incorporated herein by reference, discloses a single column distillation. Alternative embodiments for the acetic acid production system 100 may also be found in U.S. Pat. Nos. 6,552,221, 7,524,988, and 8,076,512, which are herein incorporated by reference.

In an embodiment, the carbonylation reaction in reactor 110 of system 100 may be performed in the presence of a catalyst. Catalysts may include, for example, rhodium catalysts and iridium catalysts.

Suitable rhodium catalysts are taught, for example, by U.S. Pat. No. 5,817,869, which is herein incorporated by reference. The rhodium catalysts may include rhodium metal and rhodium compounds. In an embodiment, the rhodium compounds may be selected from the group consisting of rhodium salts, rhodium oxides, rhodium acetates, organo-rhodium compounds, coordination compounds of rhodium, the like, and mixtures thereof in an embodiment, the rhodium compounds may be selected from the group consisting of $Rh_2$ $(CO)_4I_2$, $Rh_2$ $(CO)_4Br_2$, $Rh_2$ $(CO)_4Cl_2$, $Rh(CH_3CO_2)_2$, $Rh(CH_3CO_2)_3$, $[H]Rh(CO)_2I_2$, the like, and mixtures thereof. In an embodiment, the rhodium compounds may be selected from the group consisting of $[H]Rh$ $(CO)_2I_2$, $Rh(CH_3CO_2)_2$, the like, and mixtures thereof.

Suitable iridium catalysts are taught, for example, by U.S. Pat. No. 5,932,764. The iridium catalysts may include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)$ $4I_2]$—H+, $[Ir(CO)$ $_2Br_2]$—H+, $[IR(CO)_2I_2]$—H+, $[Ir(CH_3)I_3$ $(CO)_2]$—H+, Ir4 $(CO)1_2$, $IrCl_3·4H_2O$, $IrBr_3·4H_2O$, $Ir_3$ $(CO)1_2$, $Ir_2O_3$, $IrO_2$, $Ir(acac)(CO)_2$, $Ir(acac)_3$, $Ir(OAc)_3$, $[Ir_3O(OAc)_6$ $(H_2O)_3]$ $[OAc]$, $H_2[IrCl_6]$, the like, and mixtures thereof. In an embodiment, the iridium compounds may be selected from the group consisting of acetates, oxalates, acetoacetates, the like, and mixtures thereof. In an embodiment, the iridium compounds may be one or more acetates.

In an embodiment, the catalyst may be used with a co-catalyst. In an embodiment, co-catalysts may include metals and metal compounds selected from the group consisting of osmium, rhenium, ruthenium, cadmium, mercury, zinc, gallium, indium, and tungsten, their compounds, the like, and mixtures thereof. In an embodiment, co-catalysts may be selected from the group consisting of ruthenium compounds and osmium compounds. In an embodiment, co-catalysts may be one or more ruthenium compounds. In an embodiment, the co-catalysts may be one or more acetates.

The reaction rate depends upon the concentration of the catalyst in the reaction mixture in reactor 110. In an embodiment, the catalyst concentration may be in a range from about 1.0 mmol to about 100 mmol catalyst per liter (mmol/l) of reaction mixture. In some embodiments the catalyst concentration is at least 2.0 mmol/l, or at least 5.0 mmol/l, or at least 7.5 mmol/l. In some embodiments the catalyst concentration is at most 75 mmol/l, or at most 50 mmol/l, or at least 25 mmol/l. In particular embodiments, the catalyst concentration is from about 2.0 to about 75 mmol/l, or from about 5.0 to about 50 mmol/l, or from about 7.5 to about 25 mmol/l.

In an embodiment, the carbonylation reaction in reactor 110 of system 100 may be performed in the presence of a catalyst stabilizer. Suitable catalyst stabilizers include at least two types of catalyst stabilizers. The first type of catalyst stabilizer may be a metal iodide salt such as lithium iodide. The second type of catalyst stabilizer may be a non-salt stabilizer. In an embodiment, non-salt stabilizers may be pentavalent Group VA oxides, such as that disclosed in U.S. Pat. No. 9,790,159 which is herein incorporated by reference. In an embodiment, the catalyst stabilizer may be one or more phosphine oxides. In an embodiment, the catalyst may be CYTOP 503 from Solvay.

The one or more phosphine oxides, in one or more embodiments, are represented by the formula $R_3PO$, where R is alkyl or aryl, O is oxygen, P is phosphorous. In one or more embodiments, the one or more phosphine oxides include a compound mixture of at least four phosphine oxides, where each phosphine oxide has the formula $OPX_3$, wherein O is oxygen, P is phosphorous and X is independently selected from $C_4$-$C_{18}$ alkyls, $C_4$-$C_{15}$ aryls, $C_4$-$C_{18}$ cyclic alkyls, $C_4$-$C_{18}$ cyclic aryls and combinations thereof. Each phosphine oxide has at least 15, or at least 18 total carbon atoms.

Examples of suitable phosphine oxides for use in the compound mixture include, but are not limited to, tri-n-hexylphosphine oxide (THPO), tri-n-octylphosphine oxide (TOPO), tris(2,4,4-trimethylpentyl)-phosphine oxide, tricyclohexylphosphine oxide, tri-n-dodecylphosphine oxide, tri-n-octadecylphosphine oxide, tris(2-ethylhexyl)phosphine oxide, di-n-octylethylphosphine oxide, di-n-hexylisobutylphosphine oxide, octyldiisobutylphosphine oxide, tribenzylphosphine oxide, di-n-hexylbenzylphosphine oxide, di-n-octylbenzylphosphine oxide, 9-octyl-9-phosphabicyclo [3.3.1]nonane-9-oxide, dihexylmonooctylphosphine oxide, dioctylmonohexylphosphine oxide, dihexylmo-nodecylphosphine oxide, didecylmonohexylphosphine oxide, dioctylmonodecylphosphine oxide, didecylmonooc-tylphosphine oxide, and dihexylmonobutylphosphine oxide and the like.

The compound mixture includes from 1 wt % to 60 wt %, or from 35 wt % to 50 wt % of each phosphine oxide based on the total weight of compound mixture. In one or more specific, non-limiting embodiments, the compound mixture includes TOPO, THPO, dihexylmonooctylphosphine oxide and dioctylmonohexylphosphine oxide. For example, the compound mixture may include from 40 wt % to 44 wt % dioctylmonohexylphosphine oxide, from 28 wt % to 32 wt % dihexylmonooctylphosphine oxide, from 8 wt % to 16 wt % THPO and from 12 wt % to 16 wt % TOPO, for example.

In one or more embodiments, the compound mixture exhibits a melting point of less than 20° C., or less than 10° C., or less than 0° C., for example.

In one or more specific embodiments, the compound mixture is Cyanex™ 923, commercially available from Cytec Corporation.

The amount of pentavalent Group VA oxide, when used, is such that a ratio to rhodium is greater than about 60:1. In some embodiments, the ratio of the pentavalent Group 15 oxide to rhodium is from about 60:1 to about 500:1. In some embodiments, from about 0.1 to about 3 M of the pentava-lent Group 15 oxide may be in the reaction mixture. In some embodiments, from about 0.15 to about 1.5 M, or from 0.25 to 1.2 M, of the pentavalent Group 15 oxide may be in the reaction mixture.

In other embodiments, the reaction may occur in the absence of a stabilizer selected from the group of metal iodide salts and non-metal stabilizers such as pentavalent Group 15 oxides. In further embodiments, the catalyst stabilizer may consist of a complexing agent which is brought into contact with the reaction mixture stream 111 in the flash vessel 120.

In an embodiment, hydrogen may also be fed into the reactor 110. Addition of hydrogen can enhance the carbo-nylation efficiency. In an embodiment, the concentration of hydrogen may be in a range of from about 0.1 mol % to about 5 mol % of carbon monoxide in the reactor 110. In an embodiment, the concentration of hydrogen may be in a range of from about 0.3 mol % to about 3 mol % of carbon monoxide in the reactor 110.

In an embodiment, the carbonylation reaction in reactor 110 of system 100 may be performed in the presence of water. In an embodiment, the concentration of water is from about 2 wt % to about 14 wt % based on the total weight of the reaction mixture. In an embodiment, the water concen-tration is from about 2 wt % to about 10 wt %. In an embodiment, the water concentration is from about 4 wt % to about 8 wt %.

In an embodiment, the carbonylation reaction may be performed in the presence of methyl acetate. Methyl acetate may be formed in situ. In embodiments, methyl acetate may be added as a starting material to the reaction mixture. In an embodiment, the concentration of methyl acetate may be from about 2 wt % to about 20 wt % based on the total weight of the reaction mixture. In an embodiment, the concentration of methyl acetate may be from about 2 wt % to about 16 wt %. In an embodiment, the concentration of methyl acetate may be from about 2 wt % to about 8 wt %. Alternatively, methyl acetate or a mixture of methyl acetate and methanol from byproduct streams of the methanolysis of polyvinyl acetate or ethylene-vinyl acetate copolymers can be used for the carbonylation reaction.

In an embodiment, the carbonylation reaction may be performed in the presence of methyl iodide. Methyl iodide may be a catalyst promoter. In an embodiment, the concen-tration of MeI may be from about 0.6 wt % to about 36 wt % based on the total weight of the reaction mixture. In an embodiment, the concentration of MeI may be from about 4 wt % to about 24 wt %. In an embodiment, the concentration of MeI may be from about 6 wt % to about 20 wt %. Alternatively, MeI may be generated in the reactor 110 by adding HI.

In an embodiment, methanol and carbon monoxide may be fed to the reactor 110 in stream 112 and stream 114, respectively. The methanol feed stream to the reactor 110 may come from a syngas-methanol facility or any other source. Methanol does not react directly with carbon mon-oxide to form acetic acid. It is converted to MeI by the HI present in the reactor 110 and then reacts with carbon monoxide and water to give acetic acid and regenerate the HI.

In an embodiment, the carbonylation reaction in reactor 110 of system 100 may occur at a temperature within the range of about 120° C. to about 250° C., alternatively, about 150° C. to about 250° C., alternatively, about 150° C. to about 200° C. In an embodiment, the carbonylation reaction in reactor 110 of system 100 may be performed under a pressure within the range of about 200 psia (1.4 MPa-a) to 2000 psia (13.8 MPa-a), alternatively, about 200 psia (1,379 kPa-a) to about 1,000 psia (6.8 MPa-a), alternatively, about 300 psia (2.1 MPa-a) to about 500 psia (3.4 MPa-a).

In an embodiment, the reaction mixture may be with-drawn from the reactor 110 through stream 111 and is flashed in flash vessel 120 to form a vapor stream 126 and a liquid stream 121. The reaction mixture in stream 111 may include acetic acid, methanol, methyl acetate, methyl iodide, carbon monoxide, carbon dioxide, water, HI, heavy impurities, catalyst, or combinations thereof. The flash vessel 120 may comprise any configuration for separating vapor and liquid components via a reduction in pressure. For example, the flash vessel 120 may comprise a flash tank, nozzle, valve, or combinations thereof.

The flash vessel 120 may have a pressure below that of the reactor 110. In an embodiment, the flash vessel 120 may have a pressure of from about 10 psig (69 kPa-g) to 100 psig (690 kPa-g). In an embodiment, the flash vessel 120 may have a temperature of from about 100° C. to 160° C.

The vapor stream 126 may include acetic acid and other volatile components such as methanol, methyl acetate, methyl iodide, carbon monoxide, carbon dioxide, water, entrained HI, complexed HI, and mixtures thereof. The liquid stream 121 may include the catalyst, complexed HI, HI, an azeotrope of HI and water, and mixtures thereof. The liquid stream 121 may further comprise sufficient amounts of water and acetic acid to carry and stabilize the catalyst, non-volatile catalyst stabilizers, or combinations thereof. The liquid stream 121 may recycle to the reactor 110. The vapor stream 126 may be communicated to light-ends col-umn 130 for distillation.

In an embodiment, the vapor stream 126 may be distilled in a light-ends column 130 to form an overhead stream 132, a crude acetic acid product stream 136, and a bottom stream 131. In an embodiment, the light-ends column 130 may have at least 10 theoretical stages or 16 actual stages. In an alternative embodiment, the light-ends column 130 may have at least 14 theoretical stages. In an alternative embodi-ment, the light-ends column 130 may have at least 18 theoretical stages. In embodiments, one actual stage may equal approximately 0.6 theoretical stages. Actual stages can be trays or packing. The reaction mixture may be fed via stream 126 to the light-ends column 130 at the bottom or the first stage of the column 130.

Stream 132 may include acetaldehyde, water, carbon monoxide, carbon dioxide, methyl iodide, methyl acetate, methanol and acetic acid, and mixtures thereof. Stream 131 may have acetic acid, methyl iodide, methyl acetate, HI, water, and mixtures thereof. Stream 136 may have acetic acid, HI, water, heavy impurities, and mixtures thereof.

In an embodiment, the light-ends column 130 may be operated at an overhead pressure within the range of 20 psia (138 kPa-a) to 40 psia (276 kPa-a), alternatively, the overhead pressure may be within the range of 30 psia (207 kPa-a) to 35 psia (241 kPa-a). In an embodiment, the overhead temperature may be within the range of 95° C. to 135° C., alternatively, the overhead temperature may be within the range of 110° C. to 135° C., alternatively, the overhead temperature may be within the range of 125° C. to 135° C. In an embodiment, the light-ends column 130 may be operated at a bottom pressure within the range of 25 psia (172 kPa-a) to 45 psia (310 kPa-a), alternatively, the bottom pressure may be within the range of 30 psia (207 kPa-a) to 40 psia (276 kPa-a).

In an embodiment, the bottom temperature may be within the range of 115° C. to 155° C., alternatively, the bottom temperature is within the range of 125° C. to 135° C. In an embodiment, crude acetic acid in stream 136 may be emitted from the light-ends column 140 as a liquid side-draw. Stream 136 may be operated at a pressure within the range of 25 psia (172 kPa-a) to 45 psia (310 kPa-a), alternatively, the pressure may be within the range of 30 psia (207 kPa-a) to 40 psia (276 kPa-a). In an embodiment, the temperature of stream 136 may be within the range of 110° C. to 140° C., alternatively, the temperature may be within the range of 125° C. to 135° C. Stream 136 may be taken between the fifth to the eighth actual stage of the light-ends column 130.

In one or more embodiments, the crude acetic acid in stream 136 may be optionally subjected to further purification, such as, but not limited to, drying-distillation, in drying column 140 to remove water and heavy-ends distillation in stream 141. Stream 141 may be communicated to heavy-ends column 150 where heavy impurities such as propionic acid may be removed in stream 151 and final acetic acid product may be recovered in stream 156.

The overhead stream 132 from the light-ends column 130 may be condensed and separated in a decanter 134 to form a light aqueous phase and a heavy organic phase. In some embodiments, a portion or all of the heavy organic phase may be sent as stream 138 for further processing, as discussed below. In some embodiments, a portion or all of the light aqueous phase may be sent as stream 139 for further processing, as discussed below. In some embodiments, a portion or all of the heavy organic phase may be sent as stream 138 and a portion or all of the light aqueous phase may be sent as stream 139 for further processing, as discussed below. Further, a portion of stream 138 and/or stream 139 may be optionally recycled to the reactor 110 via stream 112, for example. It should be noted that the portion of stream 138 and/or 139 sent for further processing (FIG. 1A) and the other portion of the stream 138 and/or 139, respectively, recycled to the reactor 110 may each originate as independent streams from the decanter 134 heavy organic phase and/or light aqueous phase, respectively. In some embodiments, the light aqueous phase from the decanter 134 may be recycled to the light-ends column 130 in stream 135 or may be recycled to the reactor 110 in stream 139 via stream 112, for example.

The heavy organic phase stream 138 may have acetaldehyde, MeI, methyl acetate, acetic acid, water, and mixtures thereof. In an embodiment, stream 138 may be essentially non-aqueous with a water concentration of less than 1 wt %. In an embodiment, stream 138 may have MeI greater than 50% by weight of the stream. The light aqueous phase in streams 135 and 139 may have water (greater than 50% by weight of the stream), acetic acid, methyl acetate, methyl iodide, acetaldehyde, and mixtures thereof. Make-up water may be introduced into the decanter 134 via an external source.

Decanter Effluent Distillation

Figure 1A:
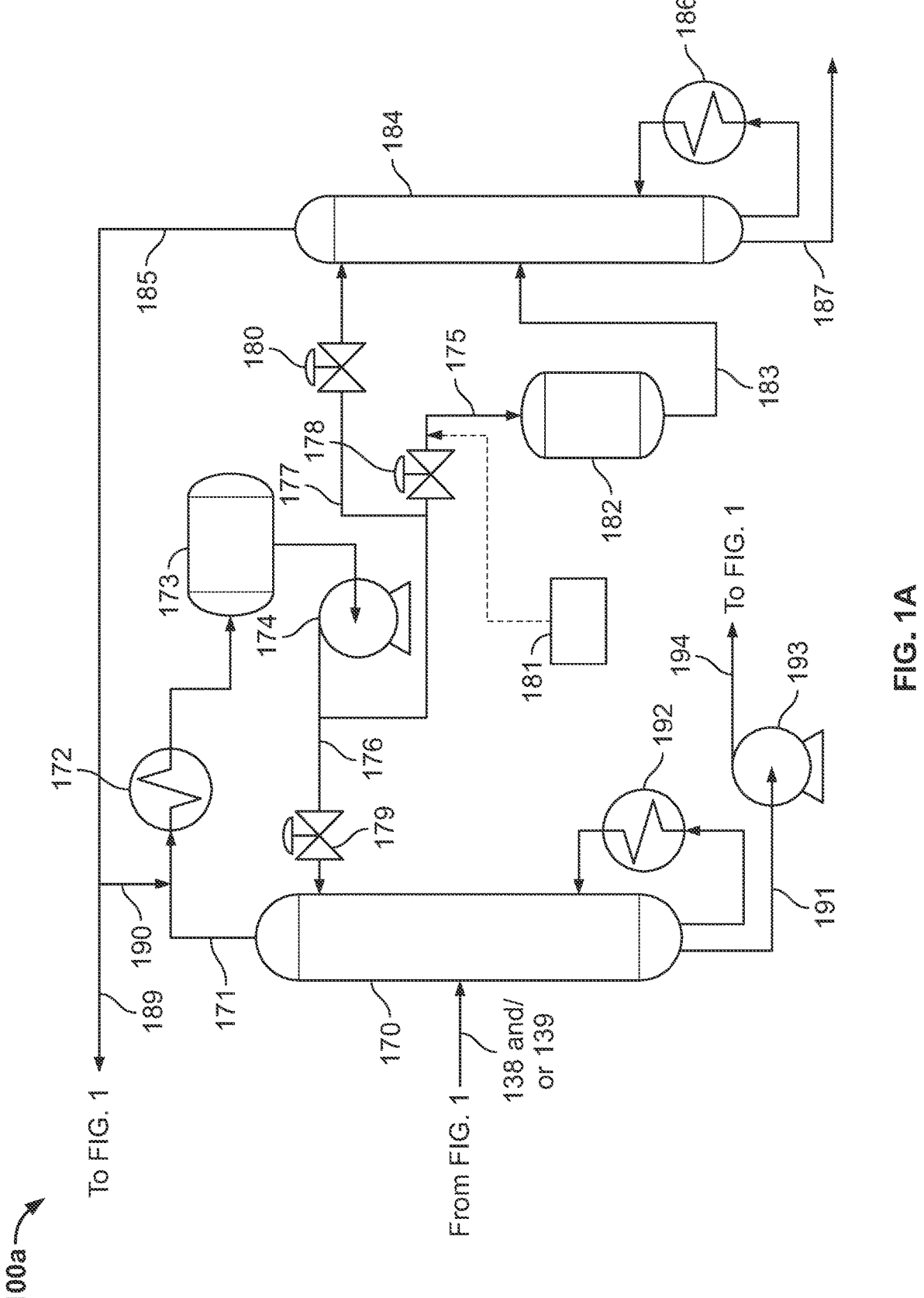
FIG. 1A is a schematic of an exemplary continuation of FIG. 1 in accordance with embodiments of the present techniques.

In some embodiments, as shown in FIG. 1A, at least a portion of the heavy organic phase from the decanter 134 is sent via stream 138 to a decanter effluent distillation column 170. In some embodiments, at least a portion of the light aqueous phase from the decanter 134 is sent via stream 139 to a decanter effluent distillation column 170. In some embodiments, at least a portion of the heavy organic phase and at least a portion of the light aqueous phase are sent via streams 138 and 139, respectively, to a decanter effluent distillation column 170. Due to the different constituents of the heavy organic phase and the light aqueous phase, physical dimensions and internals of decanter effluent distillation column 170, based on the selected feed, such a slipstream of the heavy organic phase, a slipstream of the light aqueous phase, or a range of ratios of the heavy organic phase and the light aqueous phase. In decanter effluent distillation column 170, acetaldehyde is separated from higher boiling components, such as, but not limited to methyl acetate, water, and acetic acid. In one example of a decanter effluent distillation column, the stream 138 is distilled to form a vapor stream comprising over 50%, over 80%, or over 90%, of the acetaldehyde from the heavy organic phase 138, the light aqueous phase 139, or the combination thereof, from the decanter 134 and a bottoms stream comprising over 50%, over 80%, or over 90%, of the methyl iodide, over 50%, over 80%, or over 90%, of the methyl acetate, over 50%, over 80%, or over 90%, of water, and over 50%, over 80%, or over 90%, of acetic acid, from the heavy organic phase 138, the light aqueous phase 139, or the combination thereof, from the decanter 134.

The overhead temperature of the distillation in the decanter effluent distillation column 170 is below about 80° C., 75° C., or 70° C. so that the vapor stream 171 comprises less than 20 wt %, less than 15 wt %, or less than 10 wt % of light alkanes. As used herein, "light alkanes" refers to linear and/or branched alkanes having six or less carbon atoms. In particular examples, the overhead vapor stream 171 temperature of the distillation is within the range of about 43° C. (boiling point of MeI) to about 80° C., about 43° C. to about 75° C., or about 43° C. to about 70° C. In particular examples, the overhead vapor stream 171 be operated at a pressure within the range of 15 psig (103 kPa-g) to 35 psig (241 kPa-g), alternatively, the pressure may be within the range of 20 psig (138 kPa-g) to 30 psig (207 kPa-g). Lowering the overhead temperature of the decanter effluent distillation column 170 desirably increases the concentration of MeI in the bottoms stream 191 but may result in a larger fraction of the total acetaldehyde entering decanter effluent distillation column 170 in the bottoms stream 191. Increasing the overhead temperature of the decanter effluent distillation column 170 desirably increases the fraction of the total acetaldehyde entering decanter effluent distillation column 170 in the overhead stream 171 but may increase the concentration of MeI in the overhead stream 171. According to certain embodiments, the bottoms stream 191 is sent by pump 193 to the acetic acid production reactor 110 as a stream 194. Heat input to column 170 is provided by reboiler 192. As shown in FIG. 1A, streams 175, 176, and 177 are the same composition.

The vapor stream 171 is cooled by condenser 172 and the resulting liquid is collected in reflux drum 173. Pump 174 sends the liquid from reflux drum 173 to provide reflux for column 170, reflux for reactor effluent distillation column 184, and feed for aldehyde reactor 182, as controlled by control valves 179, 180, and 178, respectively. It should be understood that this is one illustrative embodiment of flow scheme and should not be interpreted as a limitation of this disclosure. For instance, in some embodiments, decanter effluent distillation column 170 and/or reactor effluent distillation column 184 each have a dedicated condenser, reflux drum, and reflux pump instead of both sharing vapor stream 171.

It should be noted that removal of the troublesome byproduct acetaldehyde from the acetic acid system 100 via physical or chemical techniques has occupied significant research time in the art for over a decade. This problematic byproduct and its aldehyde derivatives may unfortunately impact product purity. Acetaldehyde may also serve undesirably as a precursor to various hydrocarbons which impact decanter 134 heavy density, and as a precursor to higher alkyl iodides which may require expensive adsorption beds for their removal, for example.

As discussed below, the present techniques provide for an acid catalyzed and ion-exchange resin pathway which contains both kinetically-controlled and thermodynamically-controlled steps to convert acetaldehyde. As explained below, the initial kinetically-controlled oligomeric product, paraldehyde, has a favorably high boiling point in terms of removal by distillation but unfortunately decomposes when heated above 60° C. The thermodynamically-controlled product, crotonaldehyde (likely formed via an aldol condensation pathway), is stable to temperature and has a sufficiently high boiling point to be removed efficiently by distillation. Conditions, such as acid catalyst and resin concentration, can be tailored to facilitate rapid formation of the thermodynamically-controlled product. Acid catalyst or resin concentration and conditions can be tailored to facilitate the thermodynamically-favored crotonaldehyde to be formed rapidly and quantitatively. Crotonaldehyde, though thermally stable, may undergo a further reaction on supported catalysts to form one or more species.

Conversion of Acetaldehyde

According to the present techniques, acetaldehyde may be removed from the acetic acid system 100 by providing a stream comprising acetaldehyde from the acetic acid system 100 and contacting the stream (e.g., 175) with an acid catalyst. Upon contacting the stream 175 with the acid catalyst in acetaldehyde reactor 182, at least a portion of the acetaldehyde in the stream is converted to an aldehyde derivative having a boiling point greater than the boiling point of acetaldehyde.

In resin vessel 182, acetaldehyde undergoes rapid acid catalyzed oligomerization to form paraldehyde in an equilibrium reaction which goes to about 75% completion, for example, depending on operating conditions in the resin vessel 182. Paraldehyde has a boiling point of 124° C. and thus would be a good candidate for separation from MeI by distillation. However, paraldehyde decomposes (back to acetaldehyde) upon heating to about 60° C., for instance, and thus while paraldehyde may be the kinetically-favored product of acid catalysis, it is not very stable. Therefore, paraldehyde may not be a suitable candidate in a downstream distillation for separation from MeI.

However, if the initial and rapidly formed paraldehyde is left in contact with the acid catalyst, the paraldehyde generally converts to the thermodynamically-favored crotonaldehyde. This is likely not a direct paraldehyde to crotonaldehyde conversion but rather occurs via paraldehyde reversion to acetaldehyde followed by aldol condensation in which two molecules of acetaldehyde react together to form crotonaldehyde. Crotonaldehyde has a boiling point of 102° C. and thus is another candidate to separate from the low boiling methyl iodide. Unlike paraldehyde, however, crotonaldehyde does not generally decompose to lower boiling compounds upon heating over modest temperatures and times.

In some embodiments, the acid catalyst can be strongly acidic ion-exchange resins. As used herein, "strongly acidic" or "strong acid" refers to an acid that completely ionizes in water, including, but not limited to, hydrochloric acid, hydrobromic acid, hydroiodic acid ("HI"), sulfuric acid, nitric acid, chloric acid, and perchloric acid. Strong acids can further include mineral acids, sulfonic acids (such as para-toluene sulfonic acid and methanesulfonic acid), heteropolyacids (such as tungstosilic acid, phosphotungstic acid and phosphomolybdic acid), and any of these acids when bound to a matrix (such as Amberlyst™ 15 (available from Sigma Aldrich, St. Louis, Missouri), which is a resin with bound sulfonic acid groups). In one instance, the ion-exchange resin, such as those that may be employed in acetaldehyde reactor 182, include strongly acidic ion-exchange resins, for example, such as Amberlyst™ 15Dry. Amberlyst™ 15Dry may be manufactured as opaque beads and may have a macroreticular pore structure with hydrogen ion sites located throughout each bead. The surface area may be about 53 m²/g, the average pore diameter may be about 300 Angstroms, and the total pore volume may be about 0.40 cc/g. Amberlyst™ 15Dry may be utilized in essentially non-aqueous systems (e.g., less than 5 wt % water). Therefore, the solution may be essentially or substantially non-aqueous with use of Amberlyst™ 15Dry.

In some embodiments, contacting the solution with the ion-exchange resin (e.g., in resin vessel 182) may occur at room temperature, ambient temperature, or a temperature below the boiling point of acetaldehyde, and so on. In an embodiment, contacting the solution with the ion-exchange resin may occur for at least about 30 minutes. The mass ratio of aldehyde to ion-exchange resin may be in a range of about 0.1 to about 2.0, for example.

In some embodiments, feed stream 175 to acetaldehyde reactor 182 further include a metered stream of a hydroxyl compound 181. Suitable hydroxyl compounds for reacting with the aldehydes include alcohols, glycols, and polyols. Suitable alcohols include $C_4$ to $C_{10}$ alcohols. In some embodiments, sterically bulky alcohols, such as 2-ethyl-hexan-1-ol, 2-methylhexan-2-ol, 3-methylpentan-3-ol, 2-methylpentan-2-ol, 3-methyl-2-butanol, 2-methylbutan-2-ol, and 3-methyl-2-butanol, are selected. By "glycol," we mean any compound that has two hydroxyl groups. Suitable glycols include ethylene glycol, propylene glycol, 1,4-butanediol, 1,3-butanediol, 1,5-pentanediol, 1,6-hexanediol, 2-methyl-1,3-propanediol, 2,2-dimethyl-1,3-propanediol, cyclohexane-1,4-dimethanol, and neopentyl glycol, the like, and mixtures thereof. Suitable polyols include those which have three or more hydroxyl functional groups such as glycerin. In some embodiments, glycols are selected because they form stable cyclic acetals with aldehydes. In some embodiments, ethylene glycol is selected because it is inexpensive and readily available.

In some embodiments, the hydroxyl compound is used in an amount within the range of 1 molar equivalent to 10 or 2 molar equivalents to 5 molar equivalents of the acetaldehyde. Use of the hydroxyl compound in combination with stream 175 at 1 molar equivalent or more results in conversion of all or substantially all of the acetaldehyde in stream 175 to acetal.

In some embodiments, the hydroxyl compound is used in an amount less than 1 molar equivalent the acetaldehyde impurities. Use of the hydroxyl compound in combination with stream 175 at less than 1 molar equivalent results in partial conversion of the acetaldehyde in stream 175 to acetal while all or substantially all of the remaining acetaldehyde is converted to crotonaldehyde.

In some embodiments, the decanter effluent distillation column overhead stream 175 is contacted with the acid catalyst in acetaldehyde reactor 182, and hence the conversion of a portion of the acetaldehyde in decanter effluent distillation column overhead stream 175, occurs at a temperature in the range of from 20° C. to 135° C., or 20° C. to 50° C.

In some embodiments, the decanter effluent distillation column overhead stream 175 is contacted with the acid catalyst in acetaldehyde reactor 182, and hence the absorption of a portion of the acetaldehyde in decanter effluent distillation column overhead stream 175, occurs at a pressure in the range of from 14.7 psia (101 kPa-a) to 263 psia (1.8 MPa-a), or 14.7 psia (101 kPa-a) to 40 psia (276 kPa-a). In some embodiments, the pressure in acetaldehyde reactor 182 is greater than or equal to the vapor pressure of acetaldehyde at the temperature in acetaldehyde reactor 182.

In some embodiments, when a hydroxyl compound 181 is not added to the feed stream 175 to acetaldehyde reactor 182, effluent stream 183 from acetaldehyde reactor 182 comprises crotonaldehyde in place of all, substantially all, or a portion of the acetaldehyde in feed stream 175 to acetaldehyde reactor 182.

In some embodiments, when a hydroxyl compound 181 is added at a rate of one or more molar equivalents of the acetaldehyde in the feed stream 175 to acetaldehyde reactor 182, effluent stream 183 from acetaldehyde reactor 182 comprises acetal in place of all, substantially all, or a portion of the acetaldehyde in feed stream 175 to acetaldehyde reactor 182.

In some embodiments, when a hydroxyl compound 181 is added at a rate of less than one molar equivalent of the acetaldehyde in the feed stream 175 to acetaldehyde reactor 182, effluent stream 183 from acetaldehyde reactor 182 comprises a mixture of acetal and crotonaldehyde in place of all, substantially all, or a portion of the acetaldehyde in feed stream 175 to acetaldehyde reactor 182.

Acetaldehyde Reactor Effluent Distillation

In some embodiments, as shown in FIG. 1A, the effluent stream 183 form the acetaldehyde reactor 182 is sent to a reactor effluent distillation column 184. In reactor effluent distillation column 184, acetaldehyde is separated from higher boiling components, such as, but not limited to methyl acetate, water, and acetic acid. In one example of a reactor effluent distillation column 184, the stream 183 is distilled to form a vapor overhead stream 185, comprising methyl iodide, methyl acetate, light alkanes, acetaldehyde, and water, and a bottoms stream 187, comprising water and all or substantially all of the aldehyde derivative from the effluent stream 183 form acetaldehyde reactor 182, wherein the aldehyde derivative is crotonaldehyde, acetal, or a combination thereof.

In some embodiments, the overhead temperature of the distillation in the reactor effluent distillation column 184 is about 45° C. to about 95° C., about 55° C. to about 85° C., or about 65° C. to about 75° C. In particular examples, the overhead vapor stream 171 be operated at a pressure within the range of 15 psig (103 kPa-g) to 35 psig (241 kPa-g), alternatively, the pressure may be within the range of 20 psig (138 kPa-g) to 30 psig (207 kPa-g). Lowering the overhead temperature of the reactor effluent distillation column 184 desirably assures that all aldehyde or substantially all derivative will be concentrated in the bottoms stream 187. Increasing the overhead temperature of the reactor effluent distillation column 184 desirably decrease the amount of water sent to bottoms stream 187. According to certain embodiments, the heat input to column 184 is provided by reboiler 195.

The bottoms stream 187 from reactor effluent distillation column 184 is sent to a waste disposition or otherwise removed from acetic acid system 100. In some embodiments, operation of system 100a, as disclosed herein, results in removal 85%, 90%, or 95% of the acetaldehyde entering system 100a.

The overhead stream 185 from reactor effluent distillation column 184 is recycled to acetic acid system 100 by being sent as stream 190 to join with the overhead stream 171 from decanter effluent distillation column 170, sent as stream 189 to a low-pressure disposition such as overhead stream 132, or a combination thereof. In some embodiments, stream 189 is not included.

In one or more embodiments, the disclosed process may be performed in a continuous format. For example, two resin beds or two acetaldehyde reactors 182 may be disposed in parallel, and while one is being regenerated, the other is in operation. On the other hand, the disclosed process may be performed in a batch format. The acetaldehyde reactor 182 may be in continuous or batch operation and may include a tank of dimension and material suitable for production of acetic acid.

SUMMARY

In some aspects, methods for removing acetaldehyde from an acetic acid system are disclosed. In an embodiment, a method comprises obtaining from the acetic acid system a solution, comprising acetic acid, water, methyl acetate, methyl iodide, and acetaldehyde, wherein the acetaldehyde is present in a first concentration based on the total weight of the solution. The solution is then distilled to form a first distillation overhead stream, comprising methyl iodide and acetaldehyde, wherein the acetaldehyde is present in a second concentration based on the total weight of the first distillation overhead stream, and the second concentration is greater than the first concentration. A reactive feed stream, comprising the first distillation overhead stream, and optionally a hydroxyl compound, is contacted with an acid catalyst to form a reacted stream, wherein contacting the reactive feed stream with the acid catalyst converts at least a portion of the acetaldehyde to an aldehyde derivative having a higher boiling point than acetaldehyde.

In some embodiments, in addition to the foregoing steps of the method for removing acetaldehyde from an acetic acid system, the method further comprises removing the aldehyde derivative from the reacted stream. The removal method can include distilling the reacted stream to form a second distillation overhead stream and a second distillation bottoms stream, wherein the second distillation bottoms stream comprises a portion of the aldehyde derivative. The second distillation bottoms stream can then be discharged from the acetic acid system.

In some embodiments, in addition to the foregoing steps of the method for removing acetaldehyde from an acetic acid system, the method further comprises recycling the second distillation overhead stream within the acetic acid system. In some instances, the acetic acid system comprises an acetic acid production reactor and an acetaldehyde reactor, and the second distillation overhead stream is recycled to the acetic acid production reactor, the acetaldehyde reactor, or a combination thereof.

In some embodiments, in addition to the foregoing steps of the method for removing acetaldehyde from an acetic acid system, the acetic acid system comprises a light-ends column and a decanter, and the method further comprises feeding a light-ends overhead stream from the light-ends column to the decanter. A heavy organic phase stream and a light aqueous phase stream are withdrawn from the decanter. The heavy organic phase stream, comprises methyl iodide, acetaldehyde, water, methyl acetate, and acetic acid. The light aqueous phase stream comprises methyl iodide, acetaldehyde, water, methyl acetate, and acetic acid. A portion of the heavy organic phase and/or a portion of the light aqueous phase stream are provided as the solution to be distilled to form the first distillation overhead stream.

In other embodiments, in addition to the foregoing steps of the method for removing acetaldehyde from an acetic acid system, the method further comprises any one or any combination of the following:

(a) the aldehyde derivative is crotonaldehyde, acetal, or a combination thereof;

(b) the hydroxyl compound: i) comprises a $C_2$-$C_{10}$ diol or triol; ii) is selected from the group consisting of ethylene glycol, propylene glycol, 1,4-butanediol, 1,3-butanediol, 1,3-propanediol, 2-methyl-1,3-propanediol, 2,2-dimethyl-1,3-propanediol, cyclohexane-1,4-dimethanol, glycerin, and combinations thereof; or is selected from the group consisting of 1,3-propanediol, 2-methyl-1,3-propanediol, glycerin, and combinations thereof;

(c) the acetic acid system comprises an acetaldehyde reactor having a fixed bed comprising the acid catalyst, and the reactive feed stream is fed to the acetaldehyde reactor;

(d) the acid catalyst is an acidic ion exchange resin; and (e) the solution comprises less than 1 wt % or greater than 20 wt % water;

In some aspects, methods for producing acetic acid are disclosed. In an embodiment, a method for producing acetic acid comprises:

(a) reacting methanol and carbon monoxide in the presence of a carbonylation catalyst to form acetic acid in an acetic acid production reactor;

(b) flashing a reaction mixture discharged from the acetic acid production reactor into a vapor stream and a liquid stream, the vapor stream comprising acetic acid, water, methanol, methyl acetate, methyl iodide, and acetaldehyde;

(c) separating the vapor stream by distillation in a first distillation column into: (1) a product side stream comprising acetic acid and water; (2) a first bottoms stream; and (3) a first overhead stream comprising methyl iodide, water, methyl acetate, acetic acid, and acetaldehyde;

(d) condensing the overhead stream into: (1) a light aqueous phase stream, comprising methyl iodide, acetaldehyde, water, methyl acetate, and acetic acid; and (2) a heavy organic phase stream, comprising methyl iodide, acetaldehyde, water, methyl acetate, and acetic acid;

(e) distilling a portion of the light aqueous phase stream or a portion of the heavy organic phase stream in a second distillation column to produce a second overhead stream and a second bottoms stream;

(f) contacting a reactive feed stream, comprising the second distillation overhead stream and optionally a hydroxyl compound, with an acid catalyst to form a reacted stream, wherein contacting the reactive feed stream with the acid catalyst converts at least a portion of the acetaldehyde to an aldehyde derivative having a higher boiling point than acetaldehyde; and (g) distilling the reacted stream in a third distillation column to produce a third overhead stream, comprising methyl iodide, methyl acetate, acetaldehyde, and water, and a third bottoms stream, comprising the aldehyde derivative and water.

In other embodiments, in addition to the foregoing steps of the method for producing acetic acid, the method the method further comprises any one or any combination of the following:

(a) the aldehyde derivative comprises crotonaldehyde, acetal, or a combination thereof;

(b) the hydroxyl compound: i) comprises a $C_2$-$C_{10}$ diol or triol; ii) is selected from the group consisting of ethylene glycol, propylene glycol, 1,4-butanediol, 1,3-butanediol, 1,3-propanediol, 2-methyl-1,3-propanediol, 2,2-dimethyl-1,3-propanediol, cyclohexane-1,4-dimethanol, glycerin, and combinations thereof; or iii) is selected from the group consisting of 1,3-propanediol, 2-methyl-1,3-propanediol, glycerin, and combinations thereof;

(c) the third overhead stream is recycled to the acetaldehyde system, and in some embodiments, to the acetic acid production reactor, the second distillation column, the acetaldehyde reactor, or a combination thereof;

(d) the light aqueous phase stream comprises greater than 20 wt % water and the heavy organic phase stream comprises less than 1 wt % water; and (e) the acid catalyst is an acidic ion exchange resin.

In some aspects, acetic acid production systems are disclosed. In an embodiment, an acetic acid production system comprises:

(a) an acetic acid production reactor to react methanol and carbon monoxide in the presence of a carbonylation catalyst to form acetic acid;

(b) a flash vessel that receives a reaction mixture comprising the acetic acid from the reactor;

(c) a first distillation column that receives a vapor stream from the flash vessel;

(d) a decanter that receives a condensed first overhead stream from the distillation column;

(e) a second distillation column that receives a portion of a heavy organic phase stream or a portion of a light aqueous phase stream from the decanter;

(f) an acetaldehyde reactor that receives (1) a second condensed overhead stream, comprising methyl iodide and acetaldehyde, from the second distillation column and (2) optionally a hydroxyl compound, wherein the acetaldehyde reactor comprises an acid catalyst to convert at least a portion of the acetaldehyde to an aldehyde derivative having a higher boiling point than acetaldehyde; and (g) a third distillation column that receives an effluent from the acetaldehyde reactor.

In other embodiments, in addition to the foregoing elements of an acetic acid production system, the system comprises any one or any combination of the following:

(a) the aldehyde derivative is crotonaldehyde, acetal, or a combination thereof; and (b) the acid catalyst is an acidic ion exchange resin.

Although the disclosed process and system have been described in detail, it should be understood that various changes, substitutions and alterations can be made herein without departing from the spirit and scope of the invention as defined by the appended claims. Moreover, the scope of the present application is not intended to be limited to the particular embodiments of the processes, machines, compositions, means, methods, and/or steps described in the specification. As one of the ordinary skill in the art will readily appreciate from the present disclosure, processes, machines, compositions, means, methods, and/or steps, presently existing or later to be developed that perform substantially the same function or achieve substantially the same result as the corresponding embodiments described herein, may be utilized according to the present invention. Accordingly, the appended claims are intended to include within their scope such processes, machines, compositions, means, methods, and/or steps.

EXAMPLES

The following investigations and examples are intended to be illustrative only, and are not intended to be, nor should they be construed as, limiting the scope of the present invention in any way.

Test Methods

In Examples 1 and 2, an Aspen computer simulation (ASPEN Plus V10 steady-state simulation) of process streams and conditions was used to simulate embodiments of the invention. The simulated process flow diagram ("PFD") is shown in FIG. 1A. Flow rates in the examples are shown on a normalized parts-per-hundred (pph) basis, wherein the feed rate (138 or 139) into FIG. 1A is 100 parts.

Example 1

Example 1 demonstrates an embodiment wherein a slip-stream of the decanter heavy organic phase stream 138 is process disclosed herein. An Aspen simulated process flow diagram ("PFD") is represented by FIG. 1A. Amberlyst 15 is used as the acid catalyst in acetaldehyde reactor 182. In this PFD, the decanter effluent distillation column 170 operates with a bottoms temperature of 169° F. (76° C.) and pressure of 25 psig (172 kPa) and an overhead temperature of 150° F. (66° C.) and pressure of 25 psig (172 kPa). Process conditions and compositions for streams 138, 171, 175, 176, 177, 191, 185, and 187 are shown in TABLE 1, below. TABLE 1 shows the calculated concentration of actetaldehyde ("HAc"), methyl iodide ("MeI"), light alkanes ("LA"), methyl acetate ("MeAc"), water ("H₂O"), crotonaldehyde ("CA"), and acetic acid ("GAA") in each identified stream. The mass balance in TABLE 1 indicates 0.20 parts of HAc entering decanter effluent distillation column 170 in heavy organic phase slipstream 138 and 0.151 parts of CA exiting system 100a in the bottoms stream 187 from reactor effluent distillation column 184. This indicates that about 95% of the incoming HAc is removed by system 100a. Actual operating data for a similarly sized acetic acid system indicated an average HAc content of 2471 ppm and an average crotonaldehyde content of 107 ppm for stream 138.

TABLE 1

| Stream Attribute | Stream | | | | | | | |
|---|---|---|---|---|---|---|---|---|
| | 138 | 171 | 175 | 176 | 177 | 191 | 185 | 187 |
| Flow (100 part basis) | 100.0 | 39.5 | 2.1 | 39.3 | 4.2 | 99.8 | 6.2 | 0.187 |
| Temp. (° F.) | 100 | 150 | 138 | 138 | 138 | 169 | 154 | 245 |
| Temp. (° C.) | 38 | 66 | 59 | 59 | 59 | 76 | 68 | 118 |
| Pressure (psig) | 25 | 25 | 25 | 25 | 25 | 25 | 25 | 25 |
| Pressure (kPa-g) | 172 | 172 | 172 | 172 | 172 | 172 | 172 | 172 |
| HAc (wt %) | 0.20 | 10.4 | 10.0 | 10.0 | 10.0 | 0.0 | 7.2 | 0.01 |
| MeI (wt %) | 82.0 | 77.3 | 77.7 | 77.7 | 77.7 | 82.2 | 80.0 | 0.1 |
| LA (wt %) | 5.2 | 7.8 | 7.9 | 7.9 | 7.9 | 5.3 | 8.1 | 0.0 |
| MeAc (wt %) | 6.6 | 4.3 | 4.3 | 4.3 | 4.3 | 6.6 | 4.5 | 0.0 |
| H₂O (wt %) | 0.4 | 0.0 | 0.0 | 0.0 | 0.0 | 0.4 | 0.1 | 19.0 |
| CA (wt %) | 0.1 | 0.0 | 0.0 | 0.0 | 0.0 | 0.1 | 0.0 | 80.9 |
| GAA (wt %) | 3.5 | 0.0 | 0.0 | 0.0 | 0.0 | 3.5 | 0.0 | 0.0 |

In Example 1, decanter effluent distillation column 170 was simulated with 14 theoretical stages, and reactor effluent distillation column 184 was simulated with 15 theoretical stages. Normalized heat input to reboiler 192 was 3.00 MMBTU per 100 lb (6.97 GJ per kg) acetaldehyde removal. Normalized heat input to reboiler 186 is 0.32 MMBTU per 100 lb (744 MJ per kg) acetaldehyde removal. One of the ordinary skill in the art will readily determine actual column sizing based on this disclosure, a desired feed rate to decanter effluent distillation column 170, and a desired acetaldehyde removal rate.

Example 2

Example 2 demonstrates an embodiment wherein a slip-stream of the decanter light aqueous phase stream 139 is process disclosed herein. An Aspen simulated process flow diagram ("PFD") is represented by FIG. 1A. Amberlyst 15 is used as the acid catalyst in acetaldehyde reactor 182. In this PFD, the decanter effluent distillation column 170 operates with a bottoms temperature of 244° F. (118° C.) and pressure of 25 psig (172 kPa) and an overhead temperature of 155° F. (68° C.) and pressure of 25 psig (172 kPa). Process conditions and compositions for streams 138, 171, 175, 176, 177, 191, 185, and 187 are shown in TABLE 2, below. The mass balance in TABLE 2 indicates 0.45 pph of HAc entering decanter effluent distillation column 170 in heavy organic phase slipstream 139 and 0.35 pph of CA exiting system 100a in the bottoms stream 187 from reactor effluent distillation column 184. This indicates that about 97% of the incoming HAc is removed by system 100a. Actual operating data for a similarly sized acetic acid system indicated an average HAc content of 8530 ppm for stream 139.

19

TABLE 2

| Stream Attribute | Stream | | | | | | | |
|---|---|---|---|---|---|---|---|---|
| | 139 | 171 | 175 | 176 | 177 | 191 | 185 | 187 |
| Flow (100 part basis) | 100.0 | 78.2 | 4.8 | 77.7 | 9.5 | 99.6 | 13.8 | 0.43 |
| Temp. (° F.) | 100 | 155 | 142 | 142 | 142 | 244 | 158 | 245 |
| Temp. (° C.) | 38 | 68 | 61 | 61 | 61 | 118 | 70 | 118 |
| Pressure (psig) | 25 | 25 | 25 | 25 | 25 | 25 | 25 | 25 |
| Pressure (kPa-g) | 172 | 172 | 172 | 172 | 172 | 172 | 172 | 172 |
| HAc (wt %) | 0.45 | 10.7 | 10.2 | 10.2 | 10.2 | 0.0 | 7.4 | 0.030 |
| MeI (wt %) | 6.4 | 68.1 | 68.5 | 68.5 | 68.5 | 6.5 | 70.6 | 0.0 |
| LA (wt %) | 0.0 | 8.9 | 8.9 | 8.9 | 8.9 | 0.0 | 9.2 | 0.0 |
| MeAc (wt %) | 8.4 | 9.6 | 9.7 | 9.7 | 9.7 | 8.4 | 10.0 | 0.1 |
| $H_2O$ (wt %) | 46.9 | 0.6 | 0.7 | 0.7 | 0.7 | 47.2 | 0.7 | 19.6 |
| CA (wt %) | 0.1 | 0.0 | 0.0 | 0.0 | 0.0 | 0.1 | 0.0 | 80.3 |
| GAA (wt %) | 37.7 | 0.0 | 0.0 | 0.0 | 0.0 | 37.9 | 0.0 | 0.0 |

In Example 2, decanter effluent distillation column 170 was simulated with 11 theoretical stages, and reactor effluent distillation column 184 was simulated with 15 theoretical stages. Normalized heat input to reboiler 192 was 4.56 MMBTU per 100 lb (10.6 GJ per kg) acetaldehyde removal. Normalized heat input to reboiler 186 is 0.35 MMBTU per 100 lb (813 MJ per kg) acetaldehyde removal. One of the ordinary skill in the art will readily determine actual column sizing based on this disclosure, a desired feed rate to decanter effluent distillation column 170, and a desired acetaldehyde removal rate.

The particular embodiments disclosed above are illustrative only, as the process and system may be modified and practiced in different but equivalent manners apparent to those skilled in the art having the benefit of the teachings herein. In the event of conflict between one or more of the incorporated patents or publications and the present disclosure, the present specification, including definitions, controls. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method for removing acetaldehyde from an acetic acid system, wherein the acetic acid system comprises a light-ends column and a decanter, the method comprising:
   feeding a light-ends overhead stream from the light-ends column to the decanter;
   withdrawing from the decanter: (i) a heavy organic phase stream, comprising methyl iodide, acetaldehyde, water, methyl acetate, and acetic acid; and (ii) a light aqueous phase stream comprising methyl iodide, acetaldehyde, water, methyl acetate, and acetic acid; and

providing as a solution a portion of the heavy organic phase stream and/or a portion of the light aqueous phase stream,
   wherein the solution comprises acetic acid, water, methyl acetate, methyl iodide, and acetaldehyde, wherein the acetaldehyde is present in a first concentration based on the total weight of the solution;
   distilling the solution to form a first distillation overhead stream, comprising methyl iodide and acetaldehyde, wherein the acetaldehyde is present in a second concentration based on the total weight of the first distillation overhead stream, and the second concentration is greater than the first concentration; and
   contacting a reactive feed stream, comprising the first distillation overhead stream, and optionally a hydroxyl compound, with an acid catalyst to form a reacted stream, wherein contacting the reactive feed stream with the acid catalyst converts at least a portion of the acetaldehyde to an aldehyde derivative having a higher boiling point than acetaldehyde.

2. The method of claim 1, wherein the aldehyde derivative is crotonaldehyde, acetal, or a combination thereof.

3. The method of claim 1, wherein the hydroxyl compound comprises a $C_2$-$C_{10}$ diol or triol.

4. The method of claim 1, further comprising removing the aldehyde derivative from the reacted stream.

5. The method of claim 4, wherein removing comprises:
   distilling the reacted stream to form a second distillation overhead stream and a second distillation bottoms stream, wherein the second distillation bottoms stream comprises a portion of the aldehyde derivative; and
   discharging the second distillation bottoms stream from the acetic acid system.

6. The method of claim 5, further comprising recycling the second distillation overhead stream within the acetic acid system.

7. The method of claim 6, wherein the acetic acid system comprises an acetic acid production reactor and an acetaldehyde reactor for contacting the reactive feed stream with the acid catalyst, and the second distillation overhead stream is recycled to the acetic acid production reactor, the acetaldehyde reactor, or a combination thereof.

8. The method of claim 1, wherein the solution comprises less than 1 wt % water.

9. The method of claim 1, wherein the solution comprises greater than 20 wt % water.

10. The method of claim 1, wherein the acetic acid system comprises an acetaldehyde reactor having a fixed bed comprising the acid catalyst, and the reactive feed stream is fed to the acetaldehyde reactor.

11. The method of claim 1, wherein the acid catalyst is an acidic ion exchange resin.

* * * * *